United States Patent [19]

Heden

[11] 3,997,400
[45] Dec. 14, 1976

[54] USE OF TANKERS AS FERMENTING VATS

[75] Inventor: Carl-Göran Hedén, Solna, Sweden

[73] Assignee: Rederi AB Salenia, Stockholm, Sweden

[22] Filed: Oct. 31, 1975

[21] Appl. No.: 627,912

[30] Foreign Application Priority Data

Nov. 28, 1974 Sweden .............................. 7414953

[52] U.S. Cl. .................................. 195/32; 195/49; 21/58; 214/14; 214/152
[51] Int. Cl.$^2$ ......................................... C12B 1/00
[58] Field of Search ................ 195/28 R, 121–124, 195/1, 104, 32, 33, 82; 210/241, 152, 2–11, DIG. 21; 141/1, 387, 388; 114/74 R, 74 T; 214/14, 152; 21/58

[56] References Cited

UNITED STATES PATENTS 3,630,365  12/1971  Woodbridge et al. ............. 210/241

*Primary Examiner*—R. B. Penland
*Attorney, Agent, or Firm*—Young & Thompson

[57] ABSTRACT

Many tankers can lie idle for longer or shorter periods or can travel empty from oil consumers on the way back to the oil suppliers. The present invention is related to utilizing vessels, which for longer or shorter periods and for various reasons cannot travel with a full load, as fermenting vats for, for example, alcohol fermentation. Water supply and temperature control are easily taken care of by means of water from the surrounding sea, and disposal of the waste from fermentation can also be accomplished by direct release, since the residues from the fermentation comprise organic material which decomposes in a very short time. In this way fermentable waste, e.g. sugar cane molasses, can be loaded for example in Cuba and allowed to ferment on the way to Europe where it is directly unloaded as finished alcohol or as raw material for a distillation plant.

4 Claims, No Drawings

USE OF TANKERS AS FERMENTING VATS

Extensive use is made of fermentation in the extraction of various products, the utilization of waste, etc. In addition to the alcohol fermentation of various types of grains and fruits employed since ancient times, spent liquors from the cellulose industry are now fermented to alcohol, hydrocarbons to protein and so forth.

The rapidly increasing need for fodder protein in particular now makes microbiological protein production of interest. It has been reckoned that the rapidly increasing cost of calf fodder, about $750 per ton of skim milk and about $500 per ton whey, has opened a European market for about 0.5 million tons of microbiological protein, SCP, per year. Added to this is the long-range need to replace fish meal, about $250 per ton, and perhaps even a portion of the soya protein, about $200 per ton, which is now included in poultry and pig fodder. Fermentation processes based on methanol and on sulfite and paper waste exist where prices of about $250 per ton can be reckoned; based on sedimentation sludge it has been possible to arrive at figures as low as, about $115 per ton.

In view of the various methods of snythesis available for production of methanol, this becomes one of the most interesting raw materials. For example, it is possible to manufacture methanol from natural gas in association with larger deposits, but it can also be produced from synthesis gas which, with the aid of pyrolysis or plasma burning, can be produced from coal, household waste and surplus cellulose. As indicated by these methods the need for large fermentation plants can arise both in localities where the building of factories is quite costly and in densely populated areas where building sites are more valuable than, for example, anchorages.

To be able to accomodate large quantities of raw materials or to produce large quantities of articles of consumption, especially fodder yeast, fermentation plants must be made quite large and are therefore costly. As examples of the size of plants of present actuality, mention can be made of BP's plant in Scotland with 100,000 tons per year of yeast cultivated on paraffin substrate, ICI in Teesside with 100,000 tons per year of bacteria cultivated on methanol, Finnish Pulp and Paper, Pehilz with 10,000 tons per year of yeast cultivated on sulfite waste, Chemipetrol, Czechoslovakia with one plant for 40,000 tons per year and another for 100,000 tons per year with yeast cultivated on ethyl alcohol.

The size of the cultivating tanks varies, but volumes in the range of 200–1000 m$^3$ are not unusual. Such tanks can yield between 5,000 and 30,000 tons per year.

One difficulty is that the raw material for fermentation may arrive at various locations on various dates and thereby create transportation problems for a stationary fermentation plant. A given raw material, e.g. molasses or methanol, may exist in large quantities at a low price at one point in time at a given location, only to later be found at an entirely different location. Moving the fermentation plant from one location to the other could thus solve appreciable transportation problems. In addition, it would also be possible to reduce the risk of political disturbances.

A seasonal supply of certain raw materials, e.g. starchy agricultural waste, often makes capital intensive investment in fermentation techniques less attractive at present.

The present invention starts with this assumption and proposes the use of the tankers, especially oil tankers, as fermenting vats. Oil shipments can be irregular and thereby entail that tankers are without freighting for longer or shorter periods. Only relatively minor alterations are required to use tankers as fermentation plants, and thus a tanker which is without freighting or carries only ballast could be used for fermentation. During fermentation the tankers could even travel from a place where raw materials are taken on, e.g. Cuba for sugar cane molasses, to then unload the product in Europe while a conversion to oil freight was being carried out.

The requisite conversion devices for sterilization, temperature control, venting and harvesting could be contained in easily connected deck containers corresponding to separate tanks, which would allow great flexibility in use. It is easy to appreciate the production capacity which the tank volumes offer if one considers tht an SCP yield of 65 kg/m$^3$/day is not unrealistic. In point of fact a cultivating volume of 10 liters gives the same daily protein yield as an ox.

By their inherent construction, tankers offer space which, with minor alterations, can be converted into fermentation plants. Annular or radial tubes with numerous holes can be provided at the bottom of the tanker oil for venting and stirring the mash with so-called air lift. Tubes made from porous ceramic material or sintered metal can also be used.

Oxygenation needs and cooling demands are important for constant productivity, 3.5 g/l/hour for various carbon sources, and values from Cooney and Levine, Adv. Appl. Microbiol. 15,337 (1972) are given below:

| Carbon source | Efficiency | | Oxygen demand, mmol/l/h | Heat production, kcal/l/h |
|---|---|---|---|---|
| | g cells/ g substrate | g/cells g/oxygen | | |
| Glucose | 0.5 | 2.1 | 53 | 6.4 |
| Methanol | 0.5 | 0.7 | 150 | 18.0 |
| Methane | 0.6 | 0.2 | 560 | 67.0 |
| n-Alkane | 1.0 | 0.53 | 210 | 25.0 |

Very large quantities of heat are thus developed in fermentation and especially in aerobic fermentation. Large quantities of cooling medium must therefore be supplied in order to hold the temperature constant at an optimal level. This presents no special problems in a tanker where the cooling water can be taken in directly from the sea, pass through cooling lines in the fermentation medium or heat exchanger and be led out into the sea again. This may be done through the cover on the fermentation vessel but it is also possible to employ holes in the bottom of the tank hold and the vessel and to lead cooling water in and out in this manner.

One problem which would previously have comprised a serious obstacle to the use of tankers for fermentation is the sterilization of the fermenting medium. When working with pure, uncontaminated cultures a special sterilization technique is required, and in technical processes the sterilization is always done with steam. A steam sterilization of the spaces in the relatively thin-walled containers in an oil tanker is not possible in view of the exactitude required for fermentation. On the other hand, various chemical preparations such as betapropiolactone, ethylene oxide, formalin, etc. may be used to advantage. A mist of betapropiolactone is particularly attractive since this substance is converted upon hydrolysis to β-hydroxypropionic acid, which can serve as a carbon source for many microorganisms. A number of alcohols in relatively concentrated form can also be used as disinfectants and, in greater dilution, as substrates. For reliable killing of spores, the alcohols require special additives. The fermentation medium may, as usual, be sterilized optionally with steam or chemically.

Another problem, which is also easily solved by fermentation in tankers, is the disposal of the waste. In alcohol fermentation, for example, draff is obtained after distilling off the alcohol. This draff can be used as cattle feed to some extent, but in larger quantities it presents problems in disposal. Such draff may, however, be released in fairly large quantities into the sea without entailing any pollution problems at all since the draff quite readily acts in the sea water as a nutrient for organisms in the water, or decomposes.

It has been hereinabove disclosed how tankers can advantageously be used for fermenting, for example, sugar cane molasses from Cuba while running with only ballast condition to Europe and thusly using the transport period for fermentation. Another fermentation process, which is carried out on an increasing scale, is protein fermentation from methanol. For this type of fermentation, loading can take place at a source of natural gas. There methanol is snythesized at the same time as the energy surplus from the production of methanol can be used for producing nitrogen compounds which serve as nutritive salts for the yeast culture. The protein fermentation can be either stationary or can be carried out during transport to the locality where the end product is to be used.

EXAMPLE

A small coast tanker having a tank volume of approx. 100 m$^3$ was cleaned and sterilized by means of a betapropiolactone mist spray. 20 m$^3$ molasses from beet sugar production having a dry content of 77% by weight, a sugar content of 50% by weight, a raffinose content of 1% by weight, an ash content of 11% by weight and 18% by weight unfermentable organic substances was diluted to 80 m$^3$ and 100 kg press yeast was added.

The molasses contains considerable amounts of nitrogen and phosphorous compounds but 100 kg of ammonium phosphate was also added in order to obtain a sufficient amount of nutritive salts for the yeast.

Fermentation took place at a temperature of 27° C and said temperature was maintained with the help of a coil in which sea water was circulated. The carbon dioxide formed therewith, approx. 2 tons, was cooled to dry ice. After 38 hours' fermentation, the fermented mash was pumped over to a distillation plant where 4,800 liters of alcohol was extracted.

What I claim is:

1. A method of utilizing an oil tanker, comprising filling the tanker with oil, transporting the tanker on a body of water to place of utilization of the oil, unloading the oil from the tanker, sterilizing the interior of the tanker with a material which sterilizes as well as provides a fermentation nutrient, filling the tanker with fermentable material, fermenting said fermentable material to produce a fermentation product while transporting the tanker over a body of water to a place of utilization of the fermentation product, unloading and recovering the fermentation product from the fermentation waste, refilling the tanker with oil, and again transporting the tanker over a body of water to a place of utilization of the oil.

2. A method as claimed in claim 1, and conducting said sterilization with a member selected from the group consisting of betapropiolactone, and alcohol.

3. A method as claimed in claim 2, in which said member is a mist of betapropiolactone, whereby said betapropiolactone serves first to disinfect the interior of the tanker and then is converted upon hydrolysis during fermentation to betahydroxypropionic acid thereby to serve as a carbon source during fermentation.

4. A method as claimed in claim 2, in which said member is an alcohol in relatively concentrated form which serves as disinfectant and upon subsequent dilution as a fermentation substrate.

* * * * *